United States Patent [19]

De Biaggi

[11] 3,951,570
[45] Apr. 20, 1976

[54] PUMPING UNIT FOR EXTRACORPOREAL HAEMATIC CIRCULATION, IN PARTICULAR IN ARTIFICIAL KIDNEYS

[76] Inventor: Gianfranco De Biaggi, Via Punta 54, Mirandola, Italy

[22] Filed: Feb. 20, 1974

[21] Appl. No.: 444,202

[30] Foreign Application Priority Data
Feb. 21, 1973 Italy.............................. 4722/73
Aug. 3, 1973 Italy.............................. 4855/73

[52] U.S. Cl............................... 417/319; 417/429; 417/475

[51] Int. Cl.² ...................... F04B 9/00; F04B 35/00; F04B 43/08

[58] Field of Search................... 417/429, 319, 475; 74/665 GD, 665 H, 665 Q, 724

[56] References Cited
UNITED STATES PATENTS

| | | | |
|---|---|---|---|
| 1,557,222 | 10/1925 | Warner............................ | 417/319 X |
| 2,611,283 | 9/1952 | Askren et al.................... | 74/665 GD |
| 2,775,204 | 12/1956 | Batten et al. ...................... | 417/319 |
| 2,789,444 | 4/1957 | Winter et al. ................... | 74/665 GD |
| 2,810,305 | 10/1957 | Brinza et al....................... | 74/848 X |
| 2,988,001 | 6/1961 | D'Arcey et al. ..................... | 417/429 |
| 3,479,280 | 11/1969 | Boissevain....................... | 210/416 R |

*Primary Examiner*—C. J. Husar
*Assistant Examiner*—Richard E. Gluck
*Attorney, Agent, or Firm*—Guido Modiano; Albert Josif

[57] ABSTRACT

Pumping unit for extracorporeal haematic circulation, in artificial kidneys, comprising an adjustable speed motor arranged to drive a pair of pumps of the peristaltic type by way of a transmission system. The pumps are able to be coupled alternately to the transmission system by means of two respective electromagnetic couplings.

3 Claims, 7 Drawing Figures

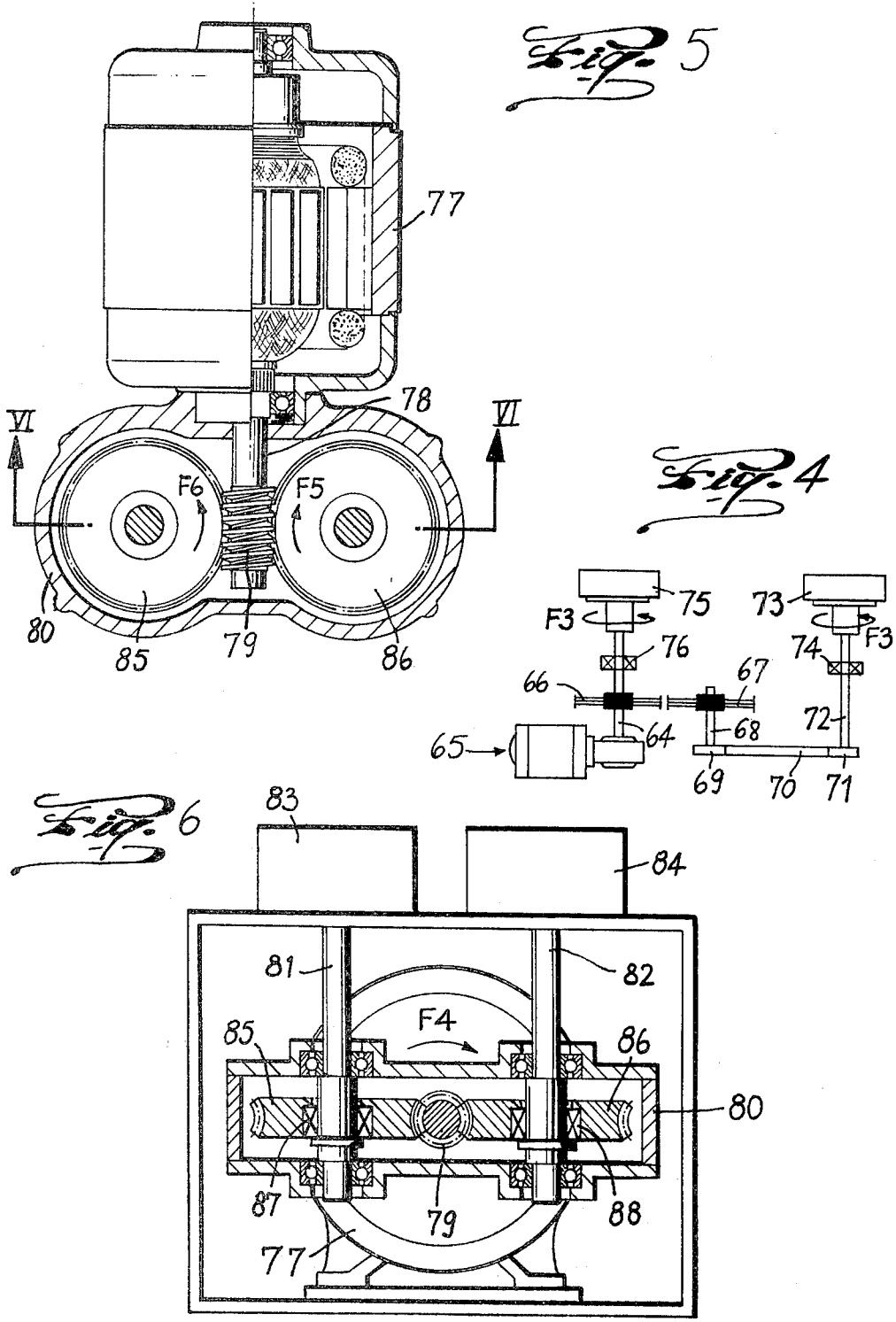

ial kidneys.

PUMPING UNIT FOR EXTRACORPOREAL HAEMATIC CIRCULATION, IN PARTICULAR IN ARTIFICIAL KIDNEYS

BACKGROUND OF THE INVENTION

This invention relates to a pumping unit for extracorporeal haematic circulation, in particular in artificial kidneys.

In extracorporeal haematic circulation in artificial kidneys, use is notably made of pumps of the peristaltic type, driven by an electric motor, which draw the blood from a point on the circulatory system (artery) and feed it, after it has been purified in the artificial kidney, into another point (vein).

These pumps are constructed in such a manner that if for any reason the electric motor should fail (for example by an interruption in the electricity supply), it is always possible to manually operate the pump by using a driving handle supplied with it. This is to ensure the continuity of the extracorporeal circulation, avoid the danger of formation of blood coagula, and obtain maximum recovery of the blood in circulation.

Known pumping units place limits on the improved utilisation of the dialyser in which, as is known, the blood yields up its impurities to the dialysis liquid through a semipermeable separation membrane. The dialyser operates in accordance with diffusion and osmosis laws and hence the passage of impurities through the semipermeable membrane depends both on the concentration gradient existing between the blood and dialysis liquid and on the pressure to which the blood is subjected with respect to the pressure of the dialysis liquid. With known pumping units it is not possible to adjust the blood pressure to the characteristics of the dialyser, also because various types of dialyser are commercially available because of which the danger of breaking the dialyser exists. Known pumping units also present disadvantages when, in haemodialysis, the technique is used of connecting an internal arterio-venous fistula to the extracorporeal circuit by means of a single needle.

Moreover the known pumping units have some drawbacks when it is necessary to add the blood with pharmaceutical products, or to provide preventing devices e.g. the so called "dripper device" adapted to shut off air formations.

SUMMARY OF THE INVENTION

The object of the present invention is consequently to provide a pumping unit which obviates the deficiencies of those at present used, in particular with reference to the improved utilisation of the dialyser and the technique with an arterio-venous fistula, of simple structure, of high reliability of operation and of economical manufacture.

The above object is attained by a pumping unit for extracorporeal haematic circulation, in particular in artificial kidneys, comprising an adjustable speed motor arranged to drive a pair of pumps of the peristaltic type by way of a transmission system, the pumps being able to be coupled alternately to the transmission system by means of two respective couplings.

BRIEF DESCRIPTION OF THE DRAWING

Further particulars will be more evident from the detailed description given hereinafter of some embodiments of the invention by way of example, illustrated in the accompanying drawings in which:

In drawing I

In drawing II FIG. 4 shows a fourth pumping unit of two pumps operable alternately in the same direction;

FIG. 5 shows a plan view of a fifth pumping unit of two pumps;

FIG. 6 is a view of the line VI—VI of the FIG. 5, and

DESCRIPTION OF THE PREFERRED EMBODIMENT

Figure 1:
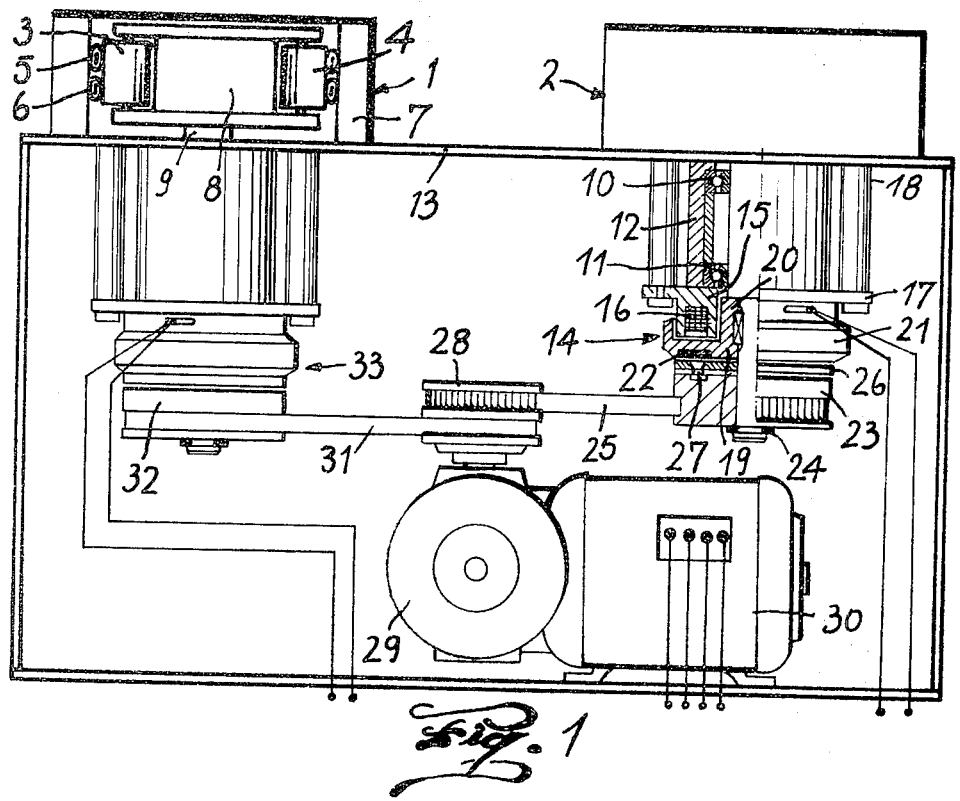
FIG. 1 shows a pumping unit composed of two pumps which can be coupled to the motor by means of electromagnetic couplings.

FIG. 1 shows two pumps of known peristaltic type, 1, 2, each comprising a pair of rollers 3, 4 which compress flexible tubes 5, 6 through which the blood circulates, against the inner semicylindrical wall of a casing 7.

The rollers 3, 4 are supported idly between the fork shaped ends of a support 8 mounted transversely on the summit of a drive shaft 9. As said shaft 9 rotates, the rollers 3, 4 roll and squeeze the flexible tubes 5, 6 so forcing the blood along this latter. The shaft 9 of the pump 2 (in the description which follows reference will be mainly made to the pump 2, the pump 1 being of an entirely similar type) is supported by rolling bearings 10, 11 coaxially with the inside of a sleeve 12. The pumps 1, 2 are fixed on the box element 13 in such a manner that the sleeves 12 project downwards inside the box element.

Hereinafter it will be supposed that the pump 1 is disposed upstream of the dialyser and draws blood from an artery, and that the pump 2 is instead disposed downstream of the dialyser and feeds blood under pressure into a vein.

At the lower end of each sleeve 12 is disposed an electromagnetic coupling indicated overall by 14 for connecting the pump 2 to the drive members. The electromagnetic coupling 14 comprises an annular body 15 in which there is a recess for housing an energising winding 16.

The body 15 is provided with a flange 17 with which legs 18 are rigid for its fixing to the upper wall of the box housing 13.

A plate 19 is keyed on to the shaft 9 which penetrates by means of a tubular portion 20 axially into the annular body 15, while a peripheral portion 21 extends externally to the body 15.

On that face of the plate 19 opposite that facing the winding 16 there is formed a seat in which is disposed a friction ring 22 made of friction material. A pulley 23 is rotatably supported on the shaft 9 and is retained axially by an elastic ring 24. The pulley 23 is provided with a rectangular race provided with teeth for engagement with a toothed belt 25.

Between the pulley 23 and plate 19 is disposed a disc 26 of ferromagnetic material, which by means of suitable rivets 27 is rotatably rigid with the pulley 23, but with respect to said pulley can make small axial strokes so as to rest on the friction ring 22 and become coupled with force to it.

The belt 25 is in the form of an endless loop about a double pulley 28 keyed on to the exit shaft of a reducer 29 flanged to an electric motor 30 which is positioned inside the box housing 13. The pulley 28 acts as an intermediate pulley also for a second toothed belt 31 in the form of an endless loop around the pulley 32 supported idly, as in the case of said pulley 23, on the shaft of the pump 1. This latter coupling between the pump 1 and drive member is also made by an electromagnetic coupling indicated overall by 33, while the relative parts and constituent elements are completely identical to those described in relation to the pump 2.

To obtain the most suitable conditions for haemodialysis the pumps are driven alternately by the motor, and their speed is adjustable by adjusting the feed voltage of the motor 30. For this purpose a manual changeover switch is provided controlled by the person responsible for controlling the haemodialysis, which alternates the energising of the couplings 14, 33. The operation of the couplings 14, 33 can also be alternated by a changeover switch controlled by a maximum and minimum pressure manometer in the haematic circuit. The speed of the motor 30 is continuously adjustable by a pair of potentiometers one of which supplies a feed voltage to the motor when it is to operate the pump 1 and the other a further feed voltage when the motor is to operate the pump 2. In this manner when changeover is made from one pump to the other, the feed voltage and hence the speed of the motor is already present and moreover it is possible to independently adjust the speeds of the pumps. The changeover from one feed voltage to the other takes place simultaneously with the changeover between the couplings 14, 33.

The operation of the pumping unit illustrated is easily understood from the description. When the motor 30 is operated the motion is transmitted towards either pump 1 or pump 2 according to whether the coupling 14 or 33 is energised. For example if a current is fed through the winding 16, a magnetic flux of toroidal development is created which closes on the ferromagnetic disc 26 and determines the axial movement of this against the friction ring 22, so providing the kinematic coupling between the shaft 9 of pump 2 and motor 30. Simultaneously the coupling 33 is deactivated. The blood is consequently drawn through the dialyser. When the pressure in the circuit of pump 2 has reached a present value, the coupling 33 is energised by means of suitable switches and the coupling 14 is de-energised, so permitting aspiration of the blood from the circulatory system. Naturally it is possible to regulate both the suction and the feed pressure by adjusting the speed of the motor 30 with a potentiometer. It is thus possible to utilise the capacity of the dialyser to act as a lung and adjust the pressure both at the point of withdrawal of the blood and at the point of feeding the blood into the circulation, so improving the conditions of exchange of the dialyser. In particular squashing is avoided at the point of withdrawal of the blood and in the dialyser, due to excessive suction.

The alternate operation of pumps 1, 2 may also be obtained by using manometers which on reaching a predetermined maximum or minimum value of pressure in the circuit of pumps 1, 2 automatically cause the operation of switches for changing over the couplings 14, 33.

One of the most important advantages of the pumping unit shown consists of the fact that the decoupling obtained by the coupling is practically istantaneous because of which when switching over from one pump to the other, the pump just shut off is prevented from continuing to rotate because of the motion of inertia of the rotating masses connected to it.

Figure 2:
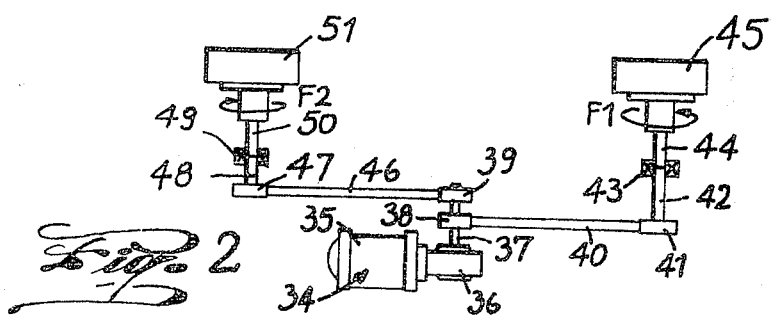
FIG. 2 shows a second pumping unit of two pumps of alternate operation in opposing directions.

With reference to FIG. 2, which shows a second embodiment of the invention, a geared motor indicated overall by 34 is shown, consisting of an electric motor 35 and a reduction gear unit 36. The electric motor is of the reversible type and its direction of rotation is controlled by a changeover switch operated manually or controlled by maximum and minimum manometers. Furthermore the speed of rotation is adjustable in one direction of rotation independently of that in the other direction by means of potentiometers which adjust the feed voltage. On the exit shaft 37 of the geared motor 34 are keyed two pulleys 38, 39. Around the pulley 38 winds a belt 40 in the form of an endless loop around the pulley 41 of a shaft 42 connected by a free wheel 43 to the shaft 44 of a peristaltic pump 45, of construction entirely similar to that of the pump 2. It is supposed that the connection between the shafts 42 and 44, i.e. the coupling of the free wheel 43, is obtained when the pump 45 rotates in the direction indicated by the arrow F1.

In an entirely similar manner, a belt 46 is wound around the pulley 39 and is looped endlessly about the pulley 47 of a shaft 48 which can be coupled by means of a free wheel 49 to the shaft 50 of a peristaltic pump 51. The connection between shafts 48, 50 is made when the pump 51 is driven in the direction of the arrow F2 which is opposite to the direction of arrow I, as clearly visible from the drawing.

From the above description it is evident that by driving the geared motor 34 in one direction or another, one of the free wheels 49, 43 becomes coupled, by which while one pump rotates the other is at rest.

Figure 3:
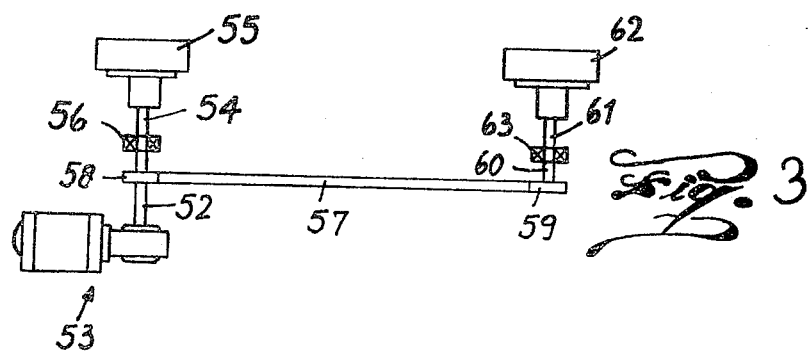
FIG. 3 shows a third pumping unit of two pumps of alternate operation in opposing directions, but contrary to those of the unit of FIG. 2.

The embodiment of FIG. 3 differs from that of FIG. 2 by the fact that the exit shaft 52 of the geared motor 53 is aligned with the shaft 54 of the pump 55 and can be coupled directly to this latter by means of the free wheel 56. The transmission of motion to the pump 55 is obtained by a belt 57 wound endlessly over pulleys 58 and 59 keyed respectively to the shaft 52 and shaft 60. The shaft 60 can be coupled to the shaft 61 of the pump 62 by means of the free wheel 63. The driving directions of free wheels 56 and 63 are like those of the embodiment of FIG. 2, i.e. opposite to each other.

The operation of the pumping unit shown in FIG. 3 is entirely similar to that of FIG. 2, even though said unit is of lesser structural complexity.

In the embodiment shown in FIG. 4, a gear wheel 66 is keyed on to the exit shaft 64 of the geared motor 65, and engages with a corresponding gear wheel 67 mounted rigidly at one end of a rotatably supported shaft 68. The shaft 68 carries at its other end a pulley 69 on which a belt 70 is wound, and looped endlessly about the pulley 71 rotatably rigid with the shaft 72 which drives the pump 73 by way of the free wheel 74. It is evident that in the pumping unit of FIG. 4 the direction of rotation F3 of the pump 75, to which the geared motor 65 transmits its motion by way of the free wheel 76, is the same as that of pump 73 because of the presence of the gear 66, 67 which reverses the motion. Like in the previous embodiments the arrow F3 indicates the driving direction of the free wheels 74 and 76.

Finally in the embodiment shown in FIGS. 5 and 6 an electric motor 77 is shown, on the exit shaft 78 of which there is a worm 79. The electric motor 77 is able to rotate in reverse directions and its speed is continuously adjustable. The shaft 78 projects into a box 80 of flat shape, flanged at its front to the ellectric motor casing. In said box 80 are rotatably supported the shafts 81, 82 of a pair of peristaltic pumps 83, 84 analogous to those of FIG. 1.

On that portion of the shafts 81, 82 inside the box 80 are supported respective helical gears 85, 86 which engage with the worm 79. The helical gears 85, 86 can be coupled to the shafts 81, 82 by free wheels 87, 88. In particular while the wheel 86 is coupled to the shaft 82 in the direction of rotation F5, the other wheel 85 is idle on the shaft 81 and vice versa.

From the description, if it is supposed that the shaft 78 rotates in the direction of the arrow F4, the gears 85, 86 are driven in the directions F5, F6. In this direction of rotation the free wheel 88 determines the coupling between the gear 86 and shaft 82, as stated, whereas the wheel 85 is idle, and thus the pump 84 is driven in the clockwise direction F5 while the pump 83 remains at rest. By reversing the direction of rotation of the motor it is evident that the pump 83 will be driven, again in the clockwise direction, while the pump 84 will be at rest because of the disengagement of the free wheel 88.

Figure 7:
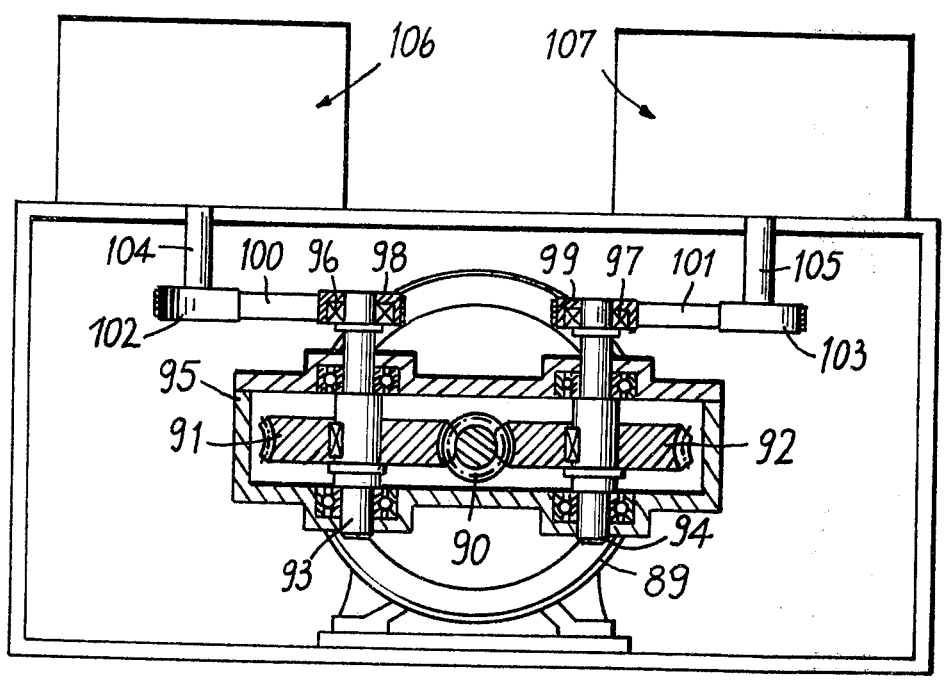
FIG. 7 is a modification of the embodiment shown in FIG. 6.

When pumps 83, 84 are of such size and width that it is not possible to arrange them close together because shafts 81, 82 are too near one another, one may assume the solution of FIG. 7.

In this solution, similarly to the solution of FIG. 6, an electric motor 89 and a worm screw 90 arranged on its outlet shaft and meshing with helical gears 91, 92 are provided. Helical gears 91, 92 are diametrally opposed with respect to shaft 90 and are coplanar and rotatably integral with shafts 93, 94 which are parallel and rotatably supported in the housing 95 integrally mounted on the frontal shield of the electric motor 89. A portion of shafts 93, 94 projects above housing 95, and these projecting portions are connectable through free-wheels 96, 97 respectively with pulleys 98, 99 on which belts 100, 101 are wound. These latter belts are also wound as a loop on respective pulleys 102, 103 keyed on the shafts 104, 105 of peristaltic pumps mounted on the upper surface of the envelope 108 accomodating the electric motor 89 and said drive members 90 – 105.

Realizing that only one of the free-wheels 96, 97 is operative for one direction of rotation of the electric motor 89 i.e. that the free wheels are active for opposite directions of rotation of the worm screw 90 of the motor 89, the operation of the pumping unit of FIG. 7 will be intuitively exactly alike that of FIG. 6.

Many variations and modifications of the invention will be apparent: e.g. in the embodiment of FIG. 7, the free-wheels instead of being arranged in the seats of pulleys 98, 99 should be arranged in the seats of the pulleys 102, 103 or again in the seats of worm gears 91, 92, as in the embodiment of FIG. 6.

Advantageously the reversal of the electric motor is actuated by a pressure gauge which senses the pressure of "a dripper" arranged downstream the dialyser and upstream the suction pump and comprising a vessel in which the blood coming from the dialyser, is dripped from above and is sucked by the suction pump.

I claim:

1. A pumping unit for extra corporeal haematic circulation, in particular in artificial kidneys, comprising a pair of pumps of the peristaltic type, an adjustable speed reversible motor, a transmission system for transmitting rotation from said motor to said pumps, said transmission system including between said motor and one of said pumps a first unidirectional coupling and between said motor and the other of said pumps a second unidirectional coupling, only said first unidirectional coupling being adapted to transmit rotation to the pump connected therewith when the motor rotates in one direction and only the other of said unidirectional couplings being adapted to transmit rotation to the other respective pump connected therewith when the motor rotates in the other direction, wherein said motor has a driving shaft extending into a housing mounted on said motor and wherein said transmission system comprises a worm gear on said driving shaft, a pair of helical gears arranged in said housing and intermeshing with said worm gear in diametrically opposite positions thereof, said helical gears lying in the same plane, a pair of parallel transmission shafts rotatably supported in said housing and each supporting one respective of said helical gears, said pair of pumps being connected with said transmission shafts, said unidirectional couplings being arranged between said helical gears and said pumps.

2. A pumping unit according to claim 1, wherein said unidirectional couplings are arranged between said helical gears and said transmission shafts.

3. A pumping unit according to claim 1, wherein said transmission system further comprises a belt transmission between each of said transmission shafts and the respective pump and wherein said unidirectional couplings are arranged between said belt transmission and said transmission shafts.

* * * * *